United States Patent [19]

Nakatani

[11] Patent Number: 5,228,778
[45] Date of Patent: Jul. 20, 1993

[54] HEAT ANALYZER

[75] Inventor: Rintaro Nakatani, Tokyo, Japan

[73] Assignee: Seiko Instruments Inc., Tokyo, Japan

[21] Appl. No.: 914,103

[22] Filed: Jul. 16, 1992

[30] Foreign Application Priority Data

Jul. 16, 1991 [JP] Japan ................................. 3-175626

[51] Int. Cl.$^5$ .......................................... G01K 17/00
[52] U.S. Cl. ........................................ 374/33; 374/11; 374/14
[58] Field of Search ....................... 374/10, 11, 14, 31, 374/33, 43, 142

[56] References Cited

U.S. PATENT DOCUMENTS

| 3,271,993 | 9/1966 | Paulik et al. | 374/10 |
| 3,643,491 | 2/1972 | Dell et al. | 374/11 |
| 3,675,465 | 7/1972 | Sommer et al. | 374/11 |
| 4,329,873 | 5/1982 | Maeda | 374/33 |
| 4,838,706 | 6/1989 | Cocy et al. | 374/33 |
| 5,083,289 | 1/1992 | Kuroda et al. | 374/33 |

Primary Examiner—William A. Cuchlinski, Jr.
Assistant Examiner—G. Bradley Bennett
Attorney, Agent, or Firm—Spensley Horn Jubas & Lubitz

[57] ABSTRACT

A heat analyzer equipped to automatically perform operations necessary for protection of measured data and for restart when a problem occurs or a measurement ends and to quickly turn off all power sources by a command input manually by an operator to a system section after daily use. At least one measurement-section power source 6 which can be turned off by an associated measurement controller 5 and a system-section power source 14 which can be turned off by a system controller 11 are included. When the temperature program of every measurement controller 5 connected to the system controller 11 through data transmission paths 8a to 8c is executed, an external environment sensor 9 detects a problem, or the operator issues a command, the system controller 11 transfers information from volatile memory 10 to a nonvolatile memory 13 before commanding every measurement controller 5 to turn off the measurement-section power source 6 and providing the system-section power source 14 with a control for turning off the system-section power source.

7 Claims, 2 Drawing Sheets

HEAT ANALYZER

BACKGROUND OF THE INVENTION

The present invention relates to heat analyzers.

Heat analyzers of the prior art include the following types:

(a) Heat analyzers in which the power sources of the measurement section and system section are separate commercial power sources. It is impossible to simultaneously turn off the power sources at the measurement or system section; and (b) Heat analyzers in which the measurement section and system section use the same commercial power source and are simultaneously turned on and off. Some of these analyzers have sensors for detecting vibrations and abnormal temperature and simultaneously turn off the power sources when certain conditions occur. In this case, the power sources are turned off under certain conditions no matter what conditions exist at the system section.

Neither of the above two types of analyzers has the capability of turning off the power source, or sources, when a temperature program is completed.

It is preferable to turn off the power source, or sources, of a heat analyzer not only when a disaster such as an earthquake or other abnormal event occurs but after a measurement in ordinary use in order to achieve operational environment control, protection of the heat analyzer, and protection of measured information because the furnace is repeatedly heated and cooled in the measurement process.

As for an analyzer of type (a) according to the prior art, however, the user has to manually turn off the power sources of the measurement and system sections if a problem occurs. In modern heat analyzers, a type is popular in which a plurality of measurement sections are connected to one system section. Therefore, for the type (a) according to the prior art, turn-off of the power source must be repeated three to five times. As for the type (b) heat analyzer according to the prior art, however, the equipment cost increases because special wiring (100 V, 50 A) from a general commercial power source is necessary instead of the wiring (100 V, 15 A) required when a plurality of measurement sections are connected since one commercial power source is used. Moreover, the power source is turned off in case of a problem no matter what condition the system section is under. This means that the power source is turned off while information necessary for the system section remains in the volatile memory in which it is being processed. Therefore, the measurement results stored by that time are lost or necessary information is erased at restart after the abnormality is corrected.

Moreover, in both types (a) and (b) according to the prior art, the power sources must manually be turned off after measurement is completed. Because thermal analysis generally takes a long time, the user has to wait for the measurement to be completed, even if this requires waiting long after the end of the normal workday.

SUMMARY OF THE INVENTION

It is an object of the present invention to obviate the above-stated problems.

A more specific object of the invention is to provide an inexpensive heat analyzer which: has a low installation cost; automatically performs operations necessary for restart after a problem is remedied or at the end of measurement; turns off the power source, or sources of, the system and measurement sections at the end of operations; and quickly turns off all power sources according to instructions given to the system section by the user after daily ordinary use.

The above and other objects are achieved, according to the invention, by the provision of a heat analyzer comprising at least one measurement section, a system section, and a data transmission path connected between the system section and the measurement section, wherein the measurement section comprises:

a furnace for heating a sample;

a temperature sensor disposed for providing information indicative of the temperature of the sample;

a physical-property value sensor disposed for measuring a physical property of the sample which varies with variations in the temperature of the sample;

a measurement-section power source for supplying heating power to the furnace;

a measurement controller which is connected to the furnace, the temperature sensor, the physical-property value sensor, the measuring-section power source and the data transmission path for receiving operating power from the measuring-section power source, controlling the furnace, delivering signals detected by the temperature sensor and the physical-value sensor to the data transmission path, and controlling the measuring-section power source to turn the measuring-section power source off in accordance with a command received via the transmission path or a command produced by the measurement controller so as to turn off the measuring-section power source; and means for manually turning the measuring-section power source on and off; and the system section comprises:

a system-section power source;

a volatile memory;

a system controller which is connected to the system-section power source, the volatile memory and the measurement controller via the data transmission path for controlling the measurement controller, receiving detected signals delivered by the measurement controller via the data transmission path and storing those signals in the volatile memory, for receiving operating power from the system-section power source and for controlling the system-section power source to turn off the system-section power source and terminate supply of operating power from the system-section power source; and means for manually turning the measuring-section power source on and off.

The present invention solves the above-stated problems and the heat analyzer mainly comprises a furnace, a temperature sensor, a physical value sensor, a measurement controller, a measurement-section power source, data transmission paths, a system controller, a system-section power source, an external environment sensor, a volatile memory, and a nonvolatile memory.

Using the heat analyzer, a sample is heated in the furnace controlled by the measurement controller in accordance with a temperature program stored in the measurement controller, the temperature of the sample or of a region close to the sample is measured by the temperature sensor, a physical property of the sample varying with the temperature change of the sample is measured by the physical value sensor, and the measured temperature and physical property values are transmitted to a system controller by the measurement controller through a data transmission path. The system controller stores the measured temperature and physical property values in a volatile memory to use them as measurement data.

When measurement progresses and the temperature program is completed or the temperature measured by the temperature sensor reaches a preset abnormal value, the measurement controller notifies the system controller that the temperature program is completed or a problem, or abnormal condition, is detected, instructs the measurement-section power source to turn off the power source and the measurement-section power source is turned off.

When the temperature program of every connected measurement controller is completed, or the external environment sensor detects a problem, or abnormal condition, or the user issues a command, the system controller instructs every connected measurement controller to provide the measurement-section power source with a control signal for turning off the power source, transfers the information in the volatile memory used by the system controller to the nonvolatile memory, and provides the system-section power source with a control signal for turning off the power source to turn off all the power sources.

DESCRIPTION OF THE PREFERRED EMBODIMENTS

An embodiment of the present invention is described below with reference to the accompanying drawings.

Figure 1:
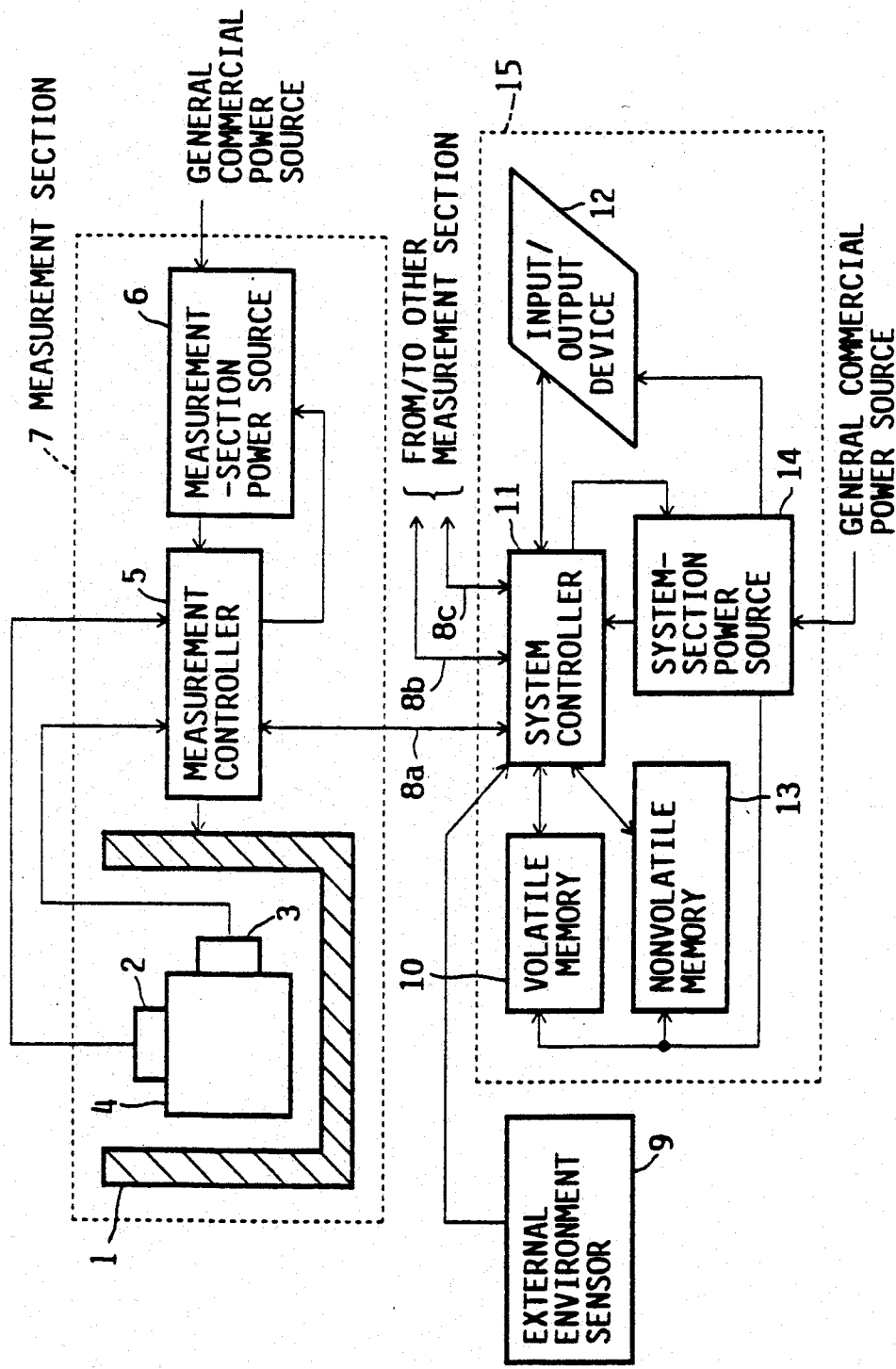
FIG. 1 is a block diagram of an embodiment of the present invention.

In FIG. 1, a measurement section 7 includes furnace 1 into which the user has previously placed a sample 4 to be measured. Sample 4 is suitably coupled with a temperature sensor 2 and a physical property value sensor 3. The physical property to be sensed may be, for example, length, weight, electrical conductivity, viscosity, physical state such as solid or liquid, etc., and sensor 3 will be selected according to the nature of the property to be sensed. A suitable gas environment may be established and maintained in furnace 1.

The user gives a command to the heat analyzer of the present invention through an input/output device 12 of a system section 15 and interactively operates the heat analyzer while watching the response outputs. Device 12 may include, as input portion, a keyboard and mouse, and, as output portion, a CRT and/or X-Y plotter.

The information necessary for measurement, including the temperature program and furnace environment composition control information inputted through the input/output device 12 by the user and a command for starting a measurement, are sent to a system controller 11 and given to a measurement controller 5 through a data transmission path 8a.

The system controller 11 controls the entire heat analyzer and has the following functions:

acceptance and interpretation of inputs sent from the input/output device 12, and output of inputted and measured results;

control of a plurality of measurement controllers 5 and reception of measured data by exchanging information with a plurality of measurement controllers 5 through data transmission paths 8a to 8c;

control of the system-section power source 14 and turn-off of the system-section power source 14 as needed; and acceptance of inputs sent from an external environment sensor 9 and judgment on whether or not the external environment is normal.

The information necessary for executing the above functions is processed in a volatile memory 10. Important information (e.g. measured data and temperature program data) is copied from volatile memory 10 to a nonvolatile memory 13 to protect the information, which is restored copying from nonvolatile memory 13 back to volatile memory 10.

Volatile memory 10 includes dynamic RAMs or static RAMs and nonvolatile memory 13 includes a hard disk, floppy disks, magneto-optic disks, or RAMs provided with a battery-backup function.

The following are information to be copied to nonvolatile memory 13:

data measured up to the present time;

information which supports or identifies the measured data, including the user's name, measurement date, measured sample name, sample weight, measured temperature program, measured load program, and results of reading data curves drawn on the basis of measured data, such as the melting temperature specified in JIS X7121 and the weight increase rate specified in JIS K7120;

the temperature program currently set in measurement controller 5 and temperature programs frequently used by users;

the load program currently set in measurement controller 5 and load program frequently used by users;

abnormal conditions or events measured by the heat analyzer, including abnormal temperature, abnormal vibration, and abnormal commercial supply voltage; and information necessary for restart. Including memory control information, program control information, and disk control information.

The data transmission paths 8a to 8c connect system controller 11 to a plurality of measurement controllers 5. Though the embodiment uses the RS-232-C interface, either digital or analog signals may be used. In the case of digital signals, an SCSI bus, VME bus, Ethernet, and GP-IB can be used. Moreover, one or more system controllers 11 can be associated with one or more measurement controllers 5.

The system-section power source 14 feeds power to each unit of the system section 15. When the user presses the power source switch to turn the power source on, power is fed to the system controller 11, volatile memory 10, nonvolatile memory 13, and input/output device 12. Thus, the system controller 11 starts the operation. Supply of power is stopped by a command from the system controller 11 or by pressing an emergency stop switch power to turn the power source off. Thus, the operation of the system controller 11 stops.

The system controller 11, volatile memory 10, nonvolatile memory 13, input/output device 12, and system-section power source 14 are housed in a single unit which is referred to as the system section 15.

The external environment sensor 9, which can be omitted for measurement, detects the environment at the location where the heat analyzer is installed, which has one or both of the following two functions:

monitoring of commercial supply voltage. The sensor monitors whether or not the commercial supply voltage lies in a range between, for example, 90 and 110 V; and monitoring of abnormal vibration. The sensor detects, for example, an earthquake and notifies the system controller 11 of occurrence of the earthquake.

Measurement controller 5 has the following functions:

control of furnace 1 in accordance with information sent from system controller 11 through data transmission paths 8a to 8c;

detection of changes in a selected physical property of sample 4 by the physical-value sensor 3 and the temperature of sample 4 by the temperature sensor 2 and transmission of the sensed values to system controller 11 through data transmission paths 8a to 8c as measured data; and control of the measurement-section power source 6 and turn-off of the measurement-section power source as needed.

Furnace 1 acts to heat sample 4 and power for heating furnace 1 is fed from measurement controller 5.

The physical-value sensor 3 detects the movement of heat quantity to the sample 4 for DSC, the weight change of the sample 4 for TG, and shape change of the sample 4 for TMA.

The measurement-section power source 6 feeds power to the measurement controller 5 when the user presses the power source switch to turn the power source on. Thus, the measurement controller 5 starts the operation of the apparatus. Supply of power is stopped by a command from the measurement controller 5 or by pressing the emergency stop switch to turn the power source off. Therefore, the measurement controller 5 stops operation.

The measurement controller 5, furnace 1, temperature sensor 2, physical-value sensor 3, and measurement-section power source 6 are housed in a single unit a set which is referred to as the measurement section 7.

The following is a further detailed description of the operation of the measurement controller 5, i.e. the measurement controller 5 connected to data transmission path 8a.

When the measurement controller 5 receives a command to start measurement, it controls the furnace 1 in accordance with the temperature program and detects a physical property value varying with the temperature change of the sample 4 by reading the physical-value sensor 3 to transmit data to the measurement controller 5.

The measurement controller 5 also receives data relating to the temperature of sample 4 measured by temperature sensor 2 and transmits that data to system controller 11 through data transmission path 8a.

During measurement, the temperature of the sample 4 measured by the temperature sensor 2 may exceed the temperature range inputted through the input/output device 12 by the user or the measurable temperature range stored in the measurement controller 5 as an initial value, i.e. the temperature reaches an abnormal value. In this case, the measurement controller 5 immediately stops measurement and notifies the system controller 11 through the data transmission path 8a that the temperature has is an abnormal value. Then, the measurement controller 5 follows the operation previously selected by the user. This operation is either of the following two:

measurement controller 5 notifies the system controller 11 of turning off of the measurement-section power source 6 through the data transmission path 8a and provides the measurement-section power source 6 with a control signal to turn off the measurement-section power source;

measurement controller 5 notifies the system controller 11 that it waiting for the next command through the data transmission path 8a and then waits for the next command.

When measurement progresses and the temperature program is completed, the measurement controller 5 notifies the system controller 11 through the data transmission path 8a that the temperature program is completed. Then, the measurement controller 5 follows the operation previously selected by the user. This operation is either of the following two:

measurement controller 5 notifies the system controller 11 of turning off the measurement-section power source 5 through the data transmission path 8a and provides the measurement-section power source 6 with a control signal to turn off the power source;

measurement controller 5 notifies the system controller 11 that it is waiting for the next command through the data transmission oath 8a and then waits for the next command.

The following is a further detailed description of the operation of the system controller 11.

The user gives information necessary for measurement to the system controller 11 and any one of the measurement controllers 5 (in this case, it is assumed that the measurement controller 5 connected to data transmission path 8a is selected) through the input/output device 12. After the information necessary for measurement is given and other preparations are completed, the user instructs the system controller 11 to start measurement. The system controller 11, having received the instruction for start of measurement, sends a command for starting measurement through the data transmission path 8a and waits for measured data sent from the measurement controller 5. When the system controller 1 receives measured data, it stores the data in the volatile memory 10.

When an abnormal environmental condition is detected by the external environment sensor 9 during measurement, the system controller 11 sends a command for turning off the measurement-section power source 6 to every connected measurement controller 5 through the data transmission paths 8a to 8c. Each measurement controller 5 which receives the command provides its associated measurement-section power source 6 with a control signal to turn off the power source under any condition. Thus, the measurement-section power source of every measurement section is turned off. Moreover, the system controller 11 copies measured data, temperature program data, and information necessary for restart from volatile memory 10 to nonvolatile memory 13 to protect that data and information. After the above operation is completed, the system controller 11 gives the system-section power source 14 a control signal to turn off the power source. The heat analyzer and operational environment are protected when a disaster or a problem occurs by a series of the above operations.

When the system controller 11 receives a notification that the temperature program is completed from every measurement controller 5 through the data transmission paths 8a to 8c without any trouble, it follows the operation previously selected by the user. This operation is either of the following two:

(1) system controller 11 sends a command for turning off the measurement-section power source 6 to every connected measurement controllers 5 through the associated one of data transmission paths 8a to 8c. The measurement controller 5 having received the command notifies the system controller 11 of turning off of the associated measurement-section power source 6 through the data transmission paths 8a to 8c and gives the associated measurement-section power source 6 a control signal to turn off the power source. When the system controller 11 receives a notification that the measurement-section power source 6 is turned off from every connected measurement controller 5 through data transmission paths 8a to 8c, it copies measured data, temperature program data, and information necessary for restart from volatile memory 10 to nonvolatile memory 13 and gives the system-section power source 14 a control signal to turn off the power source 14;

(2) system controller 11 waits for the next command from the user. In this case, when the power source 14 is to be turned off after operation ends, the user instructs the system controller 11 to turn off the power source 14 through the input/output device 12.

The user can efficiently and safely operate the heat analyzer by properly using an operation of the system controller 11 for each purpose after the temperature program is completed, that is, by selecting the operation of alternative (1) to start measurement just before he goes home, or the operation or alternative (2) to start the next measurement after a completion of the current measurement.

The user can turn off the power source of any measurement controller 5 connected to the system controller 11 at any time by instructing the system controller 11 to turn off the power source of any measurement controller 5 through the input/output device 12. The system controller 11 sends a command for turning off the measurement-section power source 6 to the selected measurement controller 5 (in this case, it is assumed that the measurement controller 5 connected to the data transmission path 8a is selected) through the data transmission path 8a. The measurement controller 5 having received the command notifies the system controller 11 of turning off of the measurement-section power source 6 through the data transmission path 8a and provides the measurement-section power source 6 with a control signal to turn off the power source.

Moreover, the user can turn off all power sources of the neat analyzer at the same time after operation ends by providing the system controller 11 with an instruction for turning off all power sources through the input/output device 12. The system controller 11 having received the instruction executes the procedure according to the above alternative (1) to turn off all power sources of the heat analyzer.

Figure 2:
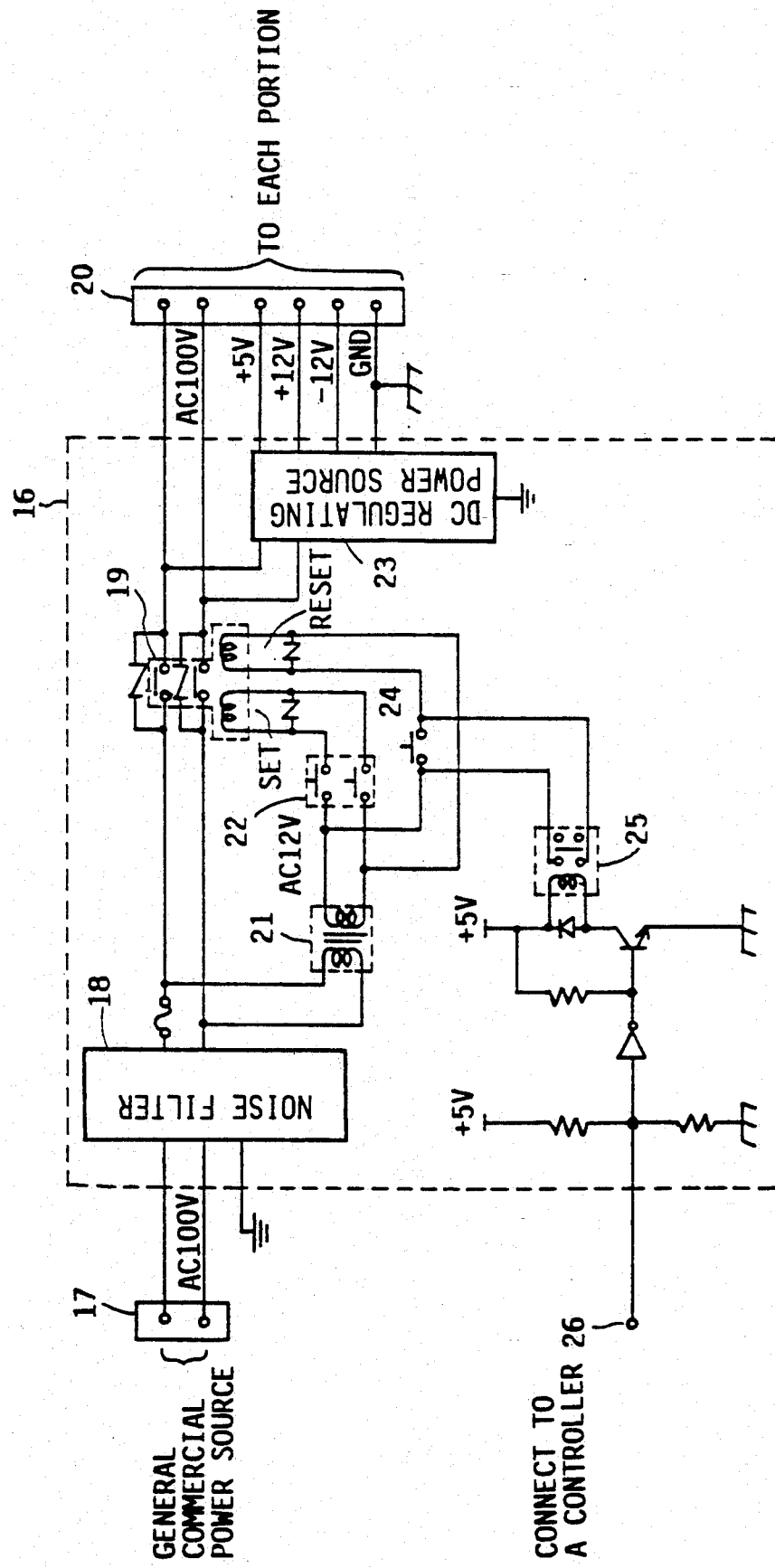
FIG. 2 is a diagram illustrating the details of an embodiment of measurement and system-section power sources according to the present invention.

Finally, an embodiment of the measurement-section power source 6 and the system-section power source 14 will be briefly described below with reference to FIG. 2.

The measurement-section power source 6 and system-section power source 14 may be constituted by identical circuits. In FIG. 2, terminal 17 is an input terminal for receiving power from a commercial power source. Noise in the power fed from the commercial power source is removed by a noise filter 18 and the power is delivered to two switchable contacts of a relay 19. Relay 19 is controlled by a coil SET and a coil RESET so that the movable contacts are closed when current flows through coil SET and are opened when current flows through coil RESET. Relay 19 maintains the switching state associated with the coil through which current flows last. That is, relay 19 keeps its movable contacts closed after current flows through coil SET and until current flows through coil RESET and keeps the contacts open after current flows through coil RESET and until current flows though coil SET. Unless a unit is being operated, the contacts of relay 19 are open and the power source is turned off.

When the user presses a switch 22 to close switch 22 and turn on the power source, the contacts of relay 19 close because a current, supplied by voltage which is stepped down to 12 VAC by a transformer 21, flows through coil SET. When the contacts of relay 19 close, AC power is directly fed to a selected connectors of a terminal 20 and DC power is fed to other connectors of terminal 20 via a DC regulating power source 23, i.e. the power source is turned on.

When the measurement controller 5 or system controller 11 delivers a control signal for turning off the associated power source, that signal is applied to a terminal 26 of the associated power supply so that terminal 26 is active. When such a signal is delivered to terminal 26, a contact of a relay 25 closes to cause current to be supplied to coil RESET of relay 19 from transformer 21. This turns the associated power supply off. Since power is no longer being supplied to the associated controller, the contact of relay 25 then opens.

If control of turning off of the power source cannot be performed due to any problem (e.g. bug in software or failure of relay 25), the user can manually turn off the power source. In this case, the contacts of relay 19 are opened by manual closing of an emergency stop switch 24 to cause current to flow through coil RESET of relay 19 and to thus turn the power source off.

A power source can be manually turned on or off by inserting or removing a plug connecting power source 17 to a mains outlet instead of providing or using the above-described turn-on switch 22 and emergency stop switch 24.

According to the present invention, as described above, a heat analyzer is so constituted that the power source of the heat analyzer is divided into a system-section power source capable of being turned off by means of a system controller and a measurement-section power source capable of being turned off by means of a measurement controller, information in a volatile memory used by the system controller is transferred to a nonvolatile memory prior to turn off the power source when a temperature program is completed, a problem is detected by an external environment sensor, and each power source is turned off either manually or automatically. Without inconsistency of information the power source can be quickly turned off when a problem occurs and the heat analyzer and operational environment can be protected on occurrence of an abnormal condition. Moreover, the power source is automatically turned off after every measurement is completed, time can be effectively used and the cost for installing the heat analyzer can be decreased.

Moreover, it will be appreciated that the basic operation of a heat analyzer according to the invention is already known in the art and that the manner of constructing and/or programming the controllers to control the various power sources will be readily apparent to those skilled in the art on the basis of the modes of operation disclosed herein.

This application relates to subject matter disclosed in Japanese Application number 3-175626, filed on Jul. 16, 1991, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed:

1. A heat analyzer comprising at least one measurement section, a system section, and a data transmission path connected between said system section and said measurement section, wherein said measurement section comprises:

a furnace for heating a sample;

a temperature sensor disposed for providing information indicative of the temperature of the sample;

a physical-property value sensor disposed for measuring a physical property of the sample which varies with variations in the temperature of the sample;

a measurement-section power source for supplying heating power to said furnace;

a measurement controller which is connected to said furnace, said temperature sensor, said physical-property value sensor, said measuring-section power source and said data transmission path for receiving operating power from said measuring-section power source, controlling said furnace, delivering signals detected by said temperature sensor and said physical-value sensor to said data transmission path, and controlling said measuring-section power source to turn said measuring-section power source off in accordance with a command received via said transmission path or a command produced by said measurement controller so as to turn off said measuring-section power source; and means for manually turning said measuring-section power source on and off; and said system section comprises:

a system-section power source;

a volatile memory;

a system controller which is connected to said system-section power source, said volatile memory and said measurement controller via said data transmission path for controlling said measurement controller, receiving detected signals delivered by said measurement controller via said data transmission path and storing those signals in said volatile memory, for receiving operating power from said system-section power source and for controlling said system-section power source to turn off said system-section power source and terminate supply of operating power from said system-section power source; and means for manually turning said measuring-section power source on and off.

2. A heat analyzer according to claim 1, wherein said measurement controller contains a temperature program for controlling heating by said furnace and acts to turn off said measurement-section power source when operation under control of the temperature program has ended.

3. A heat analyzer according to claim 2, wherein said measurement sensor acts of turn off said measurement-section power source when the temperature detected by said temperature sensor reaches a preset abnormal value.

4. A heat analyzer according to claim 1, wherein: there is a plurality of said measurement sections; in each said measurement section said measurement controller contains a temperature program for controlling heating by said furnace; and said system controller acts to turn off said system-section power source when operation under control of the temperature program in each of said measurement controllers has ended.

5. A heat analyzer according to claim 4, wherein: at least one of said power sources receives operating power from an external power supply; said analyzer further comprises an external environment sensor connected to said system controller to detect an abnormal voltage from the external power supply and abnormal vibrations experienced by said analyzer; and said system controller acts to turn off said system-section power source and to supply to said measurement controller a command for turning off said measurement-section power source when an abnormal voltage or abnormal vibrations are detected by said external environment sensor.

6. A heat analyzer according to claim 5, wherein said system section further comprises a nonvolatile memory connected to said system controller, and said system controller acts to transfer data from said volatile memory to said nonvolatile memory when said system-section power source prior to turning off said system-section power source.

7. A heat analyzer according to claim 5, wherein said system section further comprises a nonvolatile memory connected to said system controller, and said system controller acts to transfer data from said volatile memory to said nonvolatile memory when said system-section power source prior to turning off said system-section power source.

* * * * *